United States Patent [19]

Follet et al.

[11] Patent Number: 5,013,756
[45] Date of Patent: May 7, 1991

[54] CATECHOL DERIVATIVES, A PROCESS OF PREPARATION THEREOF, AND THERAPEUTICAL COMPOSITIONS CONTAINING THE SAME

[75] Inventors: Michel Follet; Marc Bonato, both of Aramon, France

[73] Assignee: Societe de Conseils de Recherches et d'Application Scientifiques (S.C.R.A.S), France

[21] Appl. No.: 356,568

[22] Filed: May 23, 1989

Related U.S. Application Data

[63] Continuation of Ser. No. 239,049, Aug. 30, 1988, abandoned, Continuation of Ser. No. 908,406, Sep. 16, 1986, abandoned.

[30] Foreign Application Priority Data

Sep. 26, 1985 [GB] United Kingdom ............... 8523776

[51] Int. Cl.$^5$ ............... A61K 31/10; A61K 31/235
[52] U.S. Cl. ............... 514/544; 514/568; 514/570; 514/712
[58] Field of Search ............... 435/124; 514/712, 544, 514/568, 570; 568/54, 46, 47, 48

[56] References Cited

U.S. PATENT DOCUMENTS

| | | | |
|---|---|---|---|
| 2,549,118 | 4/1951 | Newby | 568/46 |
| 3,148,997 | 9/1964 | Hemwall | 564/163 |
| 3,282,979 | 11/1966 | Reifschneider | 568/46 |
| 3,751,483 | 8/1973 | Cisney | 568/46 |
| 3,930,862 | 1/1976 | Tsubota | 96/73 |
| 4,120,866 | 10/1978 | Winkler | 568/38 |
| 4,661,505 | 4/1987 | Marshall et al. | 514/568 |
| 4,785,004 | 11/1988 | Von Sprecher et al. | 514/570 |

FOREIGN PATENT DOCUMENTS

| | | | |
|---|---|---|---|
| 60-260532 | 12/1985 | Japan | 568/46 |
| 301687 | 11/1954 | Switzerland | 568/46 |
| 301688 | 11/1954 | Switzerland | 568/46 |
| 301691 | 11/1954 | Switzerland | 568/46 |

OTHER PUBLICATIONS

Corey et al., JACS, 1982, 104, 1750–1754.

*Primary Examiner*—Nicholas S. Rizzo
*Assistant Examiner*—E. C. Ward
*Attorney, Agent, or Firm*—Lucas & Just

[57] ABSTRACT

This invention relates to catechol derivatives having the general formula

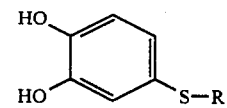

wherein R represents various substituents, to a process for the preparation of the same comprising reacting S-(3,4-dihydroxyphenyl)-isothiourea, which has the formula II, with a tosylate of the general formula III

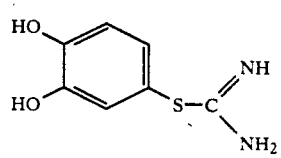

II

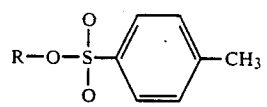

III and to therapeutical compositions wherein the active ingredient is one of these compounds.

2 Claims, No Drawings

CATECHOL DERIVATIVES, A PROCESS OF PREPARATION THEREOF, AND THERAPEUTICAL COMPOSITIONS CONTAINING THE SAME

This is a continuation of application Ser. No. 239,049 filed Aug. 30, 1988, now abandoned, which in turn is a continuation of application Ser. No. 908,406 filed Sep. 16, 1986, now abandoned.

The invention relates to catechol derivatives, to a process for their preparation and to therapeutical compositions containing the same.

The invention provides catechol derivatives having the general formula I

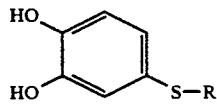

wherein

R represents a straight or branched chain acyclic hydrocarbon group having from 1 to 8 carbon atoms, one of which is optionally asymetric, a mono- or bicycloalkyl group optionally substituted by one or more alkyl groups having from 1 to 7 carbon atoms, one of the carbon atoms of the mono- or bicycloalkyl group optionally being asymetric, a phenyl group, a halophenyl group, a nitrophenyl group or a phenyl group substituted by one or more alkyl groups having from 1 to 7 carbon atoms or trifluoromethyl groups or COOY groups wherein Y stands for a hydrogen atom or an alkyl having from 1 to 5 carbon atoms.

The compounds as above defined are inhibitors of lipoxygenase and cyclooxygenase. They can be used in human therapy as non steroid antiinflammatory, antithrombotic, antiallergic, antiischemic and antianaphylactic agents.

The invention further provides a process for the preparation of said catechol derivatives, said process comprising reacting, at the reflux, in an anhydrous alkanol, S-(3,4-dihydroxy- phenyl)-isothiourea, which has the formula II below, with a tosylate of the general formula III below wherein R is as above defined.

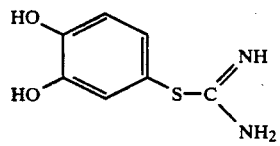

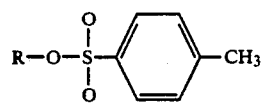

The reaction is preferably carried out by refluxing the reagents in anhydrous methanol for 48 to 72 hours under an inert atmosphere. The S-(3,4-dihydroxyphenyl)-isothiourea II is preferably employed as its hydrochloride. The group represented by R in the tosylate III may be racemic or optically active.

The S-(3,4-dihydroxyphenyl)-isothiourea II may be prepared by a method derived from that described by J. DANEKE, U. JAENKE, B. PANKOW and H.W.WANZLICK, Tetrahedron Letters 1970, 15, 1271. The tosylate III may be prepared by a method derived from that described by A. STRITWIESER Jr and A.C. WAIS Jr, J. Org. Chem., 1962, 27, 290.

The invention, finally, relates to pharmaceutical compositions using as an active ingredient therein at least of the compounds as hereinabove defined.

The following examples illustrate the invention.

EXAMPLE 1

4-(2-methylbutylthio)-catechol
(R=—$CH_2$—CH($CH_3$)—$CH_2$—$CH_3$)

22 g (0.1 mole) of S-(3,4-dihydroxyphenyl)-isothiourea were dissolved in 50 ml of anhydrous methanol in a 1 litre flask equipped with a magnetic stirrer and under a nitrogen flow. The solution was heated and a solution of sodium methoxide containing 9.2 g of sodium (4 equivalents) in 150 ml of anhydrous methanol was added. 24.2 g (0.1 mole) of 2-methylbutyl tosylate in solution in 50 ml of methanol were poured into the reaction mixture at the boiling point of methanol.

The reaction mixture was refluxed for 48 hours and the solvent was then evaporated off under reduced pressure (2000 pascals). The residue was taken up in demineralised water and acidified with 20 % hydrochloric acid. After extractions with diethyl ether, the organic phase was washed with water and then dried over anhydrous sodium sulphate. Evaporation off of the diethyl ether gave a red oil which was purified by chromatography over silica gel, using hexane: ethyl acetate (95:5 by volume) as eluant. The yield was 54 %. The identity and structure of this compound were confirmed by PMR spectroscopy and elemental microanalysis.

|              | C     | H    | O     | S     |
|--------------|-------|------|-------|-------|
| % Calculated | 62.24 | 7.60 | 15.06 | 15.10 |
| % Found      | 62.08 | 7.69 | 15.18 | 14.99 |

EXAMPLE 2

(+)-4-(2-methylbutylthio)-catechol
(R=—$CH_2$—CH($CH_3$)—$CH_2$—$CH_3$)

Working as described in example 1, but using l-2-methyl-butyl tosylate in place of 2-methyl-butyl tosylate, the title compound was obtained in a yield of 54 %. It is a yellow oil. $[\alpha]_D^{23} = +22.52$, C=0.6, chloroform. Its identity and structure were confirmed by PMR spectroscopy and elemental microanalysis.

|              | C     | H    | O     | S     |
|--------------|-------|------|-------|-------|
| % Calculated | 62.24 | 7.60 | 15.06 | 15.10 |
| % Found      | 62.21 | 7.67 | 15.22 | 15.01 |

EXAMPLE 3

4-menthylthio-catechol (R=menthyl)

Working as described in example 1, but using menthyl tosylate in place of 2-methyl-butyl tosylate, the title compound was obtained in a yield of 8 %. This compound is a solid melting at 124° C. (Kofler). Its identity and structure were confirmed by PMR spectroscopy and elemental analysis.

|   | C | H | O | S |
|---|---|---|---|---|
| % Calculated | 68.53 | 8.63 | 11.41 | 11.43 |
| % Found | 68.48 | 8.74 | 11.23 | 11.28 |

EXAMPLE 4

4-(+)-menthylthio-catechol (R=l-menthyl)

Working as described in example 1, but using l-menthyl tosylate in place of 2-methyl-butyl tosylate, the title compound was obtained in a yield of 10 %. This compound is a solid melting at 119° C. (Kofler). $[\alpha]_D^{23} = +93.98$, C=5, ethanol. Its identity and structure were confirmed by PMR spectroscopy and elemental microanalysis.

|   | C | H | O | S |
|---|---|---|---|---|
| % Calculated | 68.53 | 8.63 | 11.41 | 11.43 |
| % Found | 67.99 | 8.37 | 11.22 | 12.05 |

EXAMPLE 5

4-(1-methylheptylthio)-catechol
(R=—CH(CH$_3$)—(CH$_2$)$_5$—CH$_3$)

Working as described in example 1, but using 1-methylheptanyl tosylate in place of 2-methyl-butyl tosylate, the title compound was obtained in a yield of 26 %. This compound is an oil. Its identity and structure were confirmed by PMR spectroscopy and elemental microanalysis.

|   | C | H | O | S |
|---|---|---|---|---|
| % Calculated | 66.10 | 8.70 | 12.58 | 12.60 |
| % Found | 65.90 | 8.65 | 12.74 | 12.50 |

EXAMPLE 6

(+)-4-(1-methylheptylthio)-catechol)
(R=—CH(CH$_3$)—(CH$_2$)$_5$—CH$_3$

Working as described in example 1, but using l-1-methyl-heptyl tosylate in place of 2-methyl-butyl tosylate, the title compound was obtained in a yield of 6.5 %. This compound is an oil. $[\alpha]_D^{23} = +7$, C=0.7, chloroform. Its identity and structure were confirmed by PMR spectroscopy and elemental microanalysis.

|   | C | H | O | S |
|---|---|---|---|---|
| % Calculated | 66.10 | 8.70 | 12.58 | 12.60 |
| % Found | 65.97 | 8.68 | 12.83 | 12.71 |

EXAMPLE 7

4-phenylthio-catechol (R=phenyl)

Working as described in example 1, but using phenyl tosylate in place of 2-methyl-butyl tosylate, the title compound was obtained in a yield of 17 %. This compound is a solid melting at 164.C (Kofler). Its identity and structure were confirmed by PMR spectroscopy and elemental analysis.

|   | C | H | O | S |
|---|---|---|---|---|
| % Calculated | 66.03 | 4.62 | 14.66 | 14.69 |
| % Found | 66.00 | 4.70 | 14.64 | 14.66 |

EXAMPLE 8

4-cyclohexylthio-catechol (R=cyclohexyl)

Working as described in example 1, but using cyclohexyl tosylate in place of 2-methyl-butyl tosylate, the title compound was obtained in a yield of 31 %. This compound is a solid melting at 148.C (Kofler). Its identity and structure were confirmed by PMR spectroscopy and elemental microanalysis.

|   | C | H | O | S |
|---|---|---|---|---|
| % Calculated | 64.25 | 7.20 | 14.26 | 14.29 |
| % Found | 64.19 | 7.31 | 14.23 | 14.27 |

EXAMPLE 9

4-(3,5-dimethyl)-phenylthio-catechol
(R=-(3,5-dimethyl)-phenyl)

Working as described in example 1, but using 3,5-dimethyl-phenyl tosylate in place of 2-methyl-butyl tosylate, the title compound was obtained in a yield of 23 %. This compound is an oil. Its identity and structure were confirmed by PMR spectroscopy and elemental microanalysis.

|   | C | H | O | S |
|---|---|---|---|---|
| % Calculated | 68.26 | 5.73 | 12.99 | 13.02 |
| % Found | 68.20 | 3.93 | 12.91 | 12.96 |

EXAMPLE 10

4-(2,6-di-trifluoromethyl)-phenylthio-catechol)
(R=2,6-di-trifluoromethyl)-phenyl)

Working as described in example 1, but using (2,6-di-trifluoromethyl)-phenyl tosylate in place of 2-methylbutyl tosylate, the title compound was obtained in a yield of 13 %. This compound is a solid melting at 110° C. (Kofler). Its identity and structure were confirmed by PMR spectroscopy and elemental analysis.

|   | C | H | O | S | F |
|---|---|---|---|---|---|
| % Calculated | 47.46 | 2.28 | 9.03 | 9.05 | 32.18 |
| % Found | 47.36 | 2.55 | 8.98 | 8.98 | 32.13 |

PHARMACOLOGY

Lipoxygenases (LOs) convert arachidonic acid (AA) to hydroxy derivatives and leukotrienes. These products are potent pharmacological agents with potentially important roles in inflammation and hypersensitivity disorders. Several LOs act on AA, principally
5 LO leading to leukotrienes,
12 LO leading to 12-hydroperoxyeicosatetraenoic acid (12 HPETE) and other 12 hydroxy compounds,
15 LO leading to 15 HPETE and other 15 hydroxy compounds,
and (at a lower level) 8 LO and 11 LO.

The most important products of LO pathways are leukotrienes produced by 5-LO. The suggested importance of SRS-A in asthma and anaphylactic reactions and the finding that SRS-A belonged to the leukotrienes stimulated the interest in studies of the biological interest of these substances. LTC 4 and LTD 4 (0.1 to 1.nM) caused concentration-dependant contractions of guinea pig ileum as it has been used to determine biological activity of SRS-A relation to histamine. It was found that on a molar basis histamine was 200 times less active than LTC 4, suggesting that unit of SRS-A (6 ng Hist, HCl) corresponds to approximately 0.2 pmole LTC 4.

LTC 4 and LTD 4 also increased vascular permeability in guinea pig skin and had smooth-muscle-stimulating properties identical to those previously observed for SRS-A. LTC 4 and LTD 4 play a critical role in cardiac or pulmonary micro-circulation.

LTB 4 influences leukocyte migration by causing leukocyte adhesion to the endothelium in post-capillary venules and by potent chemotactic effects. Therefore leukotrienes are important mediators in host defence mechanisms as immediate hypersensitivity reactions and acute inflammation reactions. Furthermore, the effects of some cyclooxygenase (CO) products and the leukotrienes are complementary. Thus synergism between the leukotrienes causing plasma leakage and the vasodilators PGE 2 and PGI 2 might be of importance in the formation of oedema. Furthermore, a great importance must be given to synergistic effects between the leukotrienes with thromboxane (TxA2 in bronchoconstriction. LTC 4 and LTD 4 cause a release of TxA2 in guinea pig lung AS.TxA2 is a potent constrictor of airways, its release might contribute to the bronchospasm in allergic manifestations. Furthermore, some results seem to demonstrate that some actions of PAF-Acether could be mediated by LTB 4. Non sterioidal anti-inflammatory drugs (AINS) do not prevent anaphylaxis. Conversely, they increase hypersensitivity reactions as they mobilize AA for LOs pathways. Corticosteroids (CS) prevent the release of the precursor acting by stimulating the synthesis of lipomodulin a peptid inhibitor of phospholipase A2. By inhibiting the release of AA, CS prevents formation of not only CO products but also LOs products and then leukotrienes formation.

The increased knowledge about the LOs system seems to indicate new possibilities for the development of novel and more therapeutic agents, particularly in diseases related to immediate hypersensitivity reactions such as asthma, allergy, cardiac anaphylaxis, brain ischemia and inflammation. Such drugs might be based on antagonism of end products or inhibition of enzymes involved in the generation and further transformation of the key intermediate LTA 4. A dual effect on the leukotriene pathway and the cyclooxygenase pathway might also be of value.

(1) "In vitro" screening of 7 compounds as potential inhibitors of soybean lipoxygenase a. Introduction Monohydroxy-eicosatetraenoic acids (HETEs) are quantitatively significant metabolites of arachidonic acid (AA) in a variety of mammalian cells and tissues. For example, 12-L-HETE has been identified from the platelets; 12-L-HETE from rabbit PMN; 12-L-HETE, 11-HETE and 15-HETE from guinea pig lung and rat mast cells and 5-HETE, 8-HETE, 9-HETE, 11-HETE and 12-HETE from human neutrophils. The HETEs distribution is species dependent and representative of AA metabolism catalyzed enzymatically by lipoxygenases. The possible biological roles of these products have not been completely elucidated yet. However, 12-HETE obtained from human platelets showed a chemotactic activity for human polymorphonuclear leucocytes (Siegel, M.I. et al. Proc. Natl. Acad. Sci. 77, 308-312; 1980). 5-HPETE (the hydroperoxy acid) is the precursor of the Slow Reacting Substance, a very potent smooth-muscle contracting agent which mediates symptoms of immediate hypersensitivity. Thus, it appears that inhibition of lipoxygenase could only be beneficial particularly when screening for anti-allergic or anti-inflammatory drugs. Mammalian and plant lipoxygenase (soybean) have many biochemical properties in common, and it has been demonstrated that most inhibitors of the plant enzyme also inhibit lipoxygenases derived from blood platelets or leucocytes (Baumann, J. et al., Prostaglandins 20, 627-639, 1980). Soybean lipoxygenase induces the exclusive formation of 15-HPETE (C.P.A. Van Os et al, Biochim. et Biophys. Acta 663, 177-193, 1981) and has been demonstrated to be ten times more sensitive than platelet lipoxygenase (Wallach, D.P., et al, Biochim. and Biophys. Acta 663, 361-372, 1981). In addition, 15-HETE is a potent and specific inhibitor of platelet lipoxygenase (12-HETE) which indirectly stimulates the formation of thromboxane $A_2$ (Vanderhoek, J., et al., J. Biolog. Chem. 225, 5996-5998 1980). The 15-hydroperoxy analog has also been reported to suppress pig aortic prostacyclin synthetase activity (Gryglewski, R.J. et al. Prostaglandins 12, 685-713; 1976). This inhibitory action is exerted by the production of a destructive oxidative species probably an OH radical or a species of similar activity (Weiss, S.J., et al. Blood, 53, 1191, 1979).

b. Material and methods (b1) Spectrophotometric Assay

A spectrophotometric method has been developed to determine the enzyme activity according to Corey E.J. et al. (J. Amer. Chem. Soc, 104, 1750-1752; 1982). In a final volume of 1.8 ml was mixed 0.2 M of aerated Borax buffer pH =9.00 with 500 units of soybean lipoxygenase. When inhibitors were tested, they were added in 0.6 ml at final concentrations ranging from $10^{-3}$M to $10^{-8}$M followed by a preincubation of 10 minutes at room temperature. The reaction was initiated by $10^{-4}$M arachidonic acid. Following incubation at room temperature for 90 minutes, 15-HPETE was determined by absorbance measurements at 236 nm.

(b2) Expression of the results

This method was validated with known inhibitors of lipoxygenase. For each test substance a control was included with boiled lipoxygenase in order to take into account any absorption of the compound at the wavelength used. The percentage of enzymatic activity was calculated for each concentration, and the amount of substance required to inhibit 50 % of the enzyme activity was calculated by a linear regression on a set of data points describing the log of concentration (M) % inhibition.

| Compounds | IC$_{50}$ (concentration of 50% inhibition) |
|---|---|
| 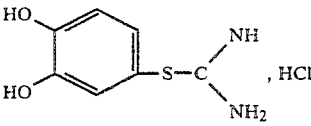 | Not active |
| 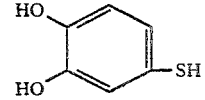 | $9.30 \cdot 10^{-5}$ M |
| 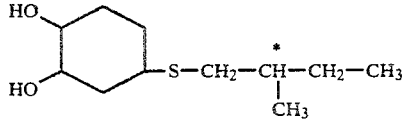 EXAMPLE 2 | $1.04 \cdot 10^{-4}$ M |
| 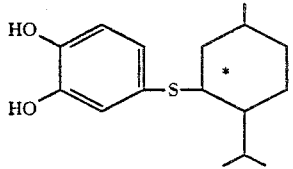 EXAMPLE 4 | $2.41 \cdot 10^{-5}$ M |
| 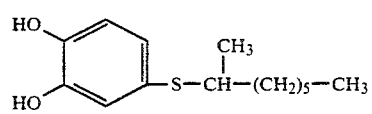 EXAMPLE 5 | $2.76 \cdot 10^{-5}$ M |
| 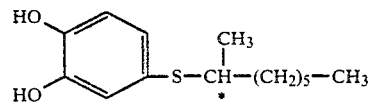 EXAMPLE 6 | $2.45 \cdot 10^{-5}$ M |
| Diphenylthiocarbazone | $1.61 \cdot 10^{-6}$ M |

(2) "In vitro" potential inhibition of superoxide anion radical ($O_2^-$)

a. Introduction

The inflammatory process is characterized by a decreased integrity of the endothelial cell barrier, vascular permeability alteration and activation of phagocytic cells such as polymorphonuclear leucocytes (PMN) with the subsequent release and generation into the extracellular space of a group of active compounds, some of which are free radicals. The relationship of these radical species to the other features of inflammation is not completely understood. An essential component of the respiratory burst of activated inflammatory cells such as PMN is the univalent enzymatic reduction of $O_2$ to the superoxide anion radical $O_2^-$. A large proportion of the generated $O_2^-$ is released into the extracellular space where spontaneous dismutation can occur with the concomittant formation of $H_2O_2$ and $O_2$. The simultaneous presence of $O_2^-$, $H_2O_2$ and chelated metal catalysts in the extracellular space can result in further generation of more active oxygen derived molecules such as hydroxyl radical (OH.) and singlet oxygen ($^1O_2$). Superoxide dismutase (SOD) functions as an enzymatic scavenger of $O_2^-$ (McCord et al. J. Biol. Chem. 244, 6049-6055 ; 1969). Whereas 1-methionine and DMSO are both OH. scavenger.

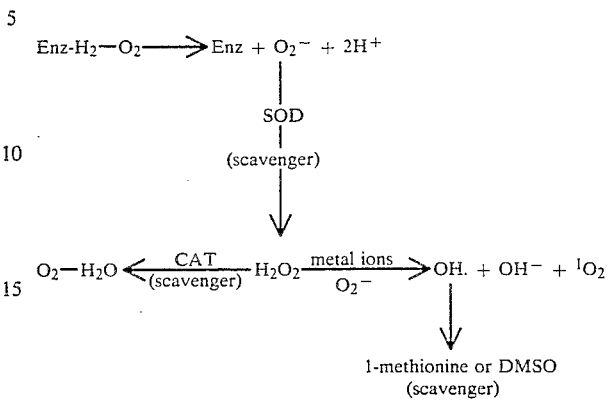

TENTATIVE MECHANISM OF SUBSTRATE-XANTHINE OXIDASE FREE RADICAL FORMATION

SCHEME 1

The substrate-xanthine oxidase model for the generation of free radicals has been intensively studied (Fridowich, I., J. Biol. Chem. 215, 4053-4057 ; 1970) and employed to generate free radicals both "in vitro" and "in vivo" (Chmori, H., et al. Biochem. Pharmacol. 27, 1397-1400 ; 1978).

A convenient and sensitive spectrophotometric assay for specifically detecting and monitoring $O_2^-$ is based on the property of this radical to reduce ferricytochrome C (Cyt $c^{3+}$). The presence of xanthine oxidase with hypoxanthine and Cyt $c^{3+}$ in bicarbonate buffer generates $O_2^-$ which initially reduces Cyt $c^{3+}$ to Cyt $c^{2+}$ (Del Maestro, R.F., Microvascular Res. 22, 255-270 1981), followed by reoxidation of some Cyt $c^{2+}$ by OH· (Fong, K., et al., Chem. Biol. Interact. 15, 77-89 ; 1976).

Hypoxanthine + Xanthine Oxidase + Cyt $c^{3+}$ ⟶

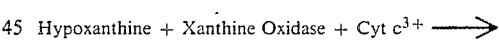
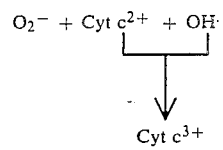

Hydrogen peroxide is formed by the two-electron reduction of molecular oxygen or by the dismutation of $O_2^-$. Catalase (CAT) reduces $H_2O_2$ to $H_2O$.

b. Material and methods

Superoxide Anion Radical $O_2^-$ Generation

The procedure followed was identical to that described by Del Maestro, R.F., J. Bjork and K.E. Arfors (Microvascular Res. 22, 239-254 ; 1981). Namely the reduction of cytochrome $c^{3+}$ (Cyt $c^{3+}$) was assayed in a system composed of 0.96 mM hypoxanthine, $5 \cdot 10^{-5}$M Cyt $c^{3+}$ in bicarbonate buffer pH=7.35 (0.132M NaCl, $4.7 \cdot 10^{-3}$M KCl, $2 \cdot 10^{-3}$M CaCl$_2$, $1.2 \cdot 10^{-3}$M MgSO$_4$, 0.018M NaHCO$_3$). The reaction was started by the addition of xanthine oxidase at a concentration of 0.07 U/ml. The increase in absorbance at 550 nm was monitored at 37° C. in a thermostated spectrophotometric cell every minute for 4 minutes.

Each test compound was added before the xanthine oxidase. A unit of activity was defined as a change of 0.001 units/minute. The percentage of enzymatic activity was calculated for each concentration of tested compounds, and the amount of substance required to inhibit 50% of the enzyme ($IC_{50}$) was calculated by a linear regression on a set of data points describing the log of concentration M/% inhibition.

c. Results

| Compounds | $O_2^-$ Scavenger $IC_{50}$ (concentration of 50% inhibition |
|---|---|
| 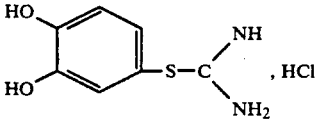 | $1.00 \ 10^{-4}$ M |
| 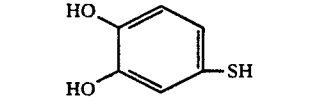 | $4.91 \ 10^{-6}$ M |
| 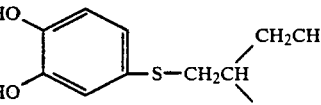  EXAMPLE 1 | $4.48 \ 10^{-6}$ M |
| 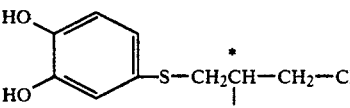  EXAMPLE 2 | $1.97 \ 10^{-5}$ M |
| 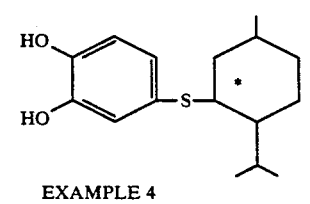  EXAMPLE 4 | $2.41 \ 10^{-5}$ M |
| 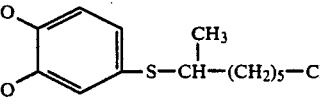  EXAMPLE 5 | $4.48 \ 10^{-6}$ M |
| 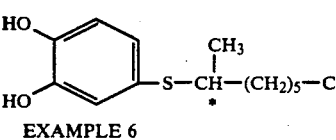  EXAMPLE 6 | $7.76 \ 10^{-5}$ M |
| Campherol | $9.05 \ 10^{-6}$ M |
| 3,4-Dihydroxyphenyl acetic acid | $3.87 \ 10^{-5}$ M |

(3) "In vitro" screening of compounds on arachidonic cascade metabolism in human platelets microsomes a. Material and methods The enzymatic assay was carried out in silanized glassware according to the procedure of P. Ho, P. Walters and H, Sullivan (Prostaglandins 12, 951 1976). The reaction mixture containing 50 mM Tris HCl buffer, pH 7.9, 5mM 2-Tryptophan, 2 M methemoglobin, 0.2 mg of microsomal powder, and the test compound in a total volume of 0.2 ml was incubated at 37° C. for 5 minutes before the addition of 10 μl of 20 $\mu M^{14}C$ arachidonic acid (0.08 μCI). After 5 minute incubation, the reaction was terminated by the addition of 10 μl of 1M citric acid.

The mixture was extracted four times with 0.5 ml of anhydrous diethyl ether and dried with sodium sulphate. The residue was resuspended in approximately 40 μl of ether and submitted to chromatography on silica gel plates. The elution system consisted of diethyl ether/methanol/acetic acid (90:1:2). The RF values were measured relative to arachidonic acid. Thin layer chromatography plates (TLC) were exposed on LKB ultrafilm for about 24 hours. Partial identification of the spots were carried out by running standards ($PGA_2$, $PGB_2$, $PGE_2$, $PGF_{2c}$, $PXB_2$, arachidonic acid) in the same solvent system. Quantitative results were obtained by scanning the developed film with a transmission densitometer (EC Apparatus 910) interfaced with a Hewlett Packard 3390A integrator. Imidazole and Indomethacin were included as positive standards for specific inhibition of thromboxane synthetase and cyclooxygenase respectively.

b. Cycloxygenase inhibition in human platelets microsomes

| Compounds | $IC_{50}$ (concentration of 50% inhibition) |
|---|---|
| 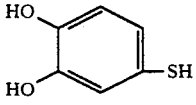 | $9.23 \ 10^{-6}$ M |
| 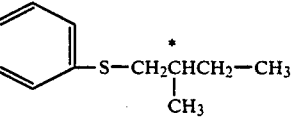  EXAMPLE 2 | $4.31 \ 10^{-6}$ M |
| 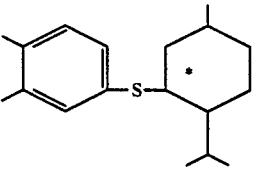  EXAMPLE 4 | $1.68 \ 10^{-5}$ M |
| 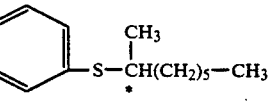  EXAMPLE 6 | $3.46 \ 10^{-6}$ M |
| Indomethacin | $1.12 \ 10^{-5}$ M |
| Phenylbutazone | $2.74 \ 10^{-4}$ M |

The activity of the substances of the cyclooxygenase is quantified by the 2 spots corresponding to $PGE_2$ and $TxB_2$ (ratio $PGE_2/TxB_2$).

(4) "In vitro" inhibition of prostaglandin synthetase in ram seminal vesicle microsomes a. Material and methods An improved assay was devised based on the published methods of Baumann et al (Naunyn-Schmiedeberg's Arch. Pharm. 307, 73 ; 1979) and Takeguchi, C. et al (Biochem. 10, 2372; 1971). The enzymatic radioassay was carried out in silanized glassware. The reaction mixture containing 50 mM Tris HCl buffer, pH=8.3, in the presence of reduced glutathione (GSH), 1 mM, as well as hydroquinone, 0.55 mM, the test compound and 50 μg of ram seminal vesicles microsomal powder in a total volume of 0.2 ml was incubated for 5 minutes at 37° C. before the addition of 10 μl of $^{14}C$ arachidonic acid $10^{-6}M$ (0.08 μCI). After 30 minutes incubation with occasional shaking, the reaction was terminated by the addition of 10 μl of citric acid 1M.

The mixture was extracted four times with 0.5 ml anhydrous diethyl ether and dried down with sodium sulphate The residue was resuspended in approximately 40 μl of ether and submitted to chromatography on silica gel plates. The elution system consisted of diethyl ether/methanol/acetic acid (45:1:2). The RF values were measured in reference to arachidonic acid. Thin layer chromatography plates were exposed on LKB ultrafilm for about 20 hours. Tentative identification of the spots was carried out by running standards ($PGE_1$, $PGE_2$, $PGF_{1a}$, $PGF_{2a}$, $PGA_1$, $PGA_2$, $PGB_1$, $PGB_2$) in the same solvent system. Quantitative results were obtained by densitometry.

b. Results

| Compounds | Autoradiographes quantification % variation | | |
|---|---|---|---|
| | $PGF_{2a}$ | $PGE_2$ | $PGD_2$ |
| 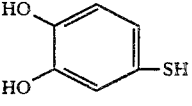 $8\ 10^{-5}$ M | +64.25 | −44.77 | −19.53 |
| 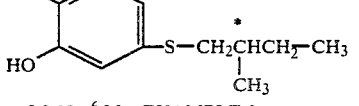 $3.2\ 10^{-6}$ M EXAMPLE 2 | +20.19 | −5.48 | +11.70 |
| 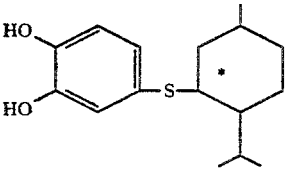 $3.2\ 10^{-6}$ M EXAMPLE 4 | −17.97 | −2.05 | −2.06 |
| Phenylbutazone $8\ 10^{-5}$ M | −43.36 | −15.37 | −21.98 |

(5) "In vitro" screening of compounds as potential inhibitors of xanthine oxidase a. Material and methods Xanthine oxidase activity was determined by the method of H.M. Kalckar (J. Biol. Chem. 167, 429–443, 1947) which measures uric acid formation spectrophotometrically.

In a spectrophotometric cuvette, xanthine oxidase was added to give a final concentration of 0.01 units/ml, followed by phosphate buffer 0.05M, pH=7.4 or the inhibitor. The reaction was started by addition of xanthine at a final concentration of $5.10^{-5}M$. The release of uric acid was monitored at 295 nm every 30 seconds for 2 minutes (linear phase). A unit of activity was defined as a change of 0.001 units/minute. The percentage of enzymatic activity was calculated for each concentration of tested compounds, and the amount of substance required to inhibit 50% of the enzyme ($IC_{50}$) was calculated by a linear regression on a set of data points describing the log of concentration M as a function of inhibition.

b. Results

| Compounds | $IC_{50}$ (concentration of 50% inhibition) |
|---|---|
| 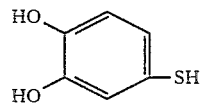 | $2.37\ 10^{-4}$ M |
| 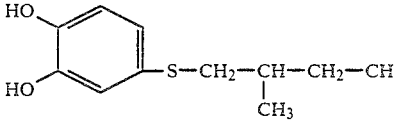 EXAMPLE 1 | $5.11\ 10^{-4}$ M |
| 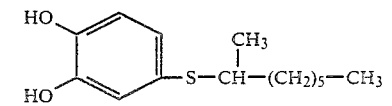 EXAMPLE 5 | $5.57\ 10^{-4}$ M |
| Folic acid | $6.76\ 10^{-7}$ M |
| Campherol | $7.89\ 10^{-6}$ M |

(6) Inhibition of human leucocytic lipoxygenase (LO)

(a) Inhibition on 5- and 12- lipoxygenases human polynuclear

Protocol for experiment No. 1:

1. Incubation of $15 \times 10^6$ human leucocytes/ml. with $Ca^{2+}2$ mM, $Mg^{2+}0.5$ mM in the presence of the inhibitors at 37° C. for 20 minutes.

2. Stimulation with 1 μg ionophore (A23187)/ml for 4 minutes.

3. Stopping of the incubation with 1 volume of methanol.

4. Analysis by RP-HPLC, colomn C18, 5 μm.

5. Measurement of the height of the peaks and comparison with the internal standard ($PGB_2$).

| Experiment No. 1: Analysis of the results | | | |
|---|---|---|---|
| | IC$_{50}$ | | |
| Products | 5-HETE | LTB$_4$ | 12-HETE |
| 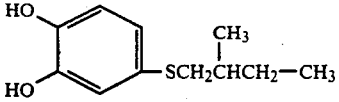 EXAMPLE 1 | $10^{-6}$ M | $10^{-6}$ M | $10^{-6}$ M |
| 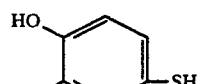 | $2 \times 10^{-6}$ M | $2 \times 10^{-6}$ M | $2 \times 10^{-6}$ M |

(b) Inhibition on 5-, 12- and 15- lipoxygenases human polynuclear

Protocol for experiment No. 2:

1. Incubation of $11 \times 10^6$ human leucocytes/ml with the inhibitors for 20 minutes (2 mM $Ca^{2+}$ and 0.5 mM $Mg^{2+}$) at 37° C.

2. Stimulation with 10 μg of arachidonic acid and 1 μg of ionophore (A23187)/ml for 4 minutes.

3. Stopping of the incubation with 1 volume of methanol and analysis by RP-HPLC.

4. Measurement of the height of the peaks and comparison with the internal standard (PGB$_2$).

| Experiment No. 2: Analysis of the results | | | | | |
|---|---|---|---|---|---|
| | IC$_{50}$ | | | | |
| Products | 5-HETE | 12-HETE | 15-HETE | HHT | LTB$_4$ |
| 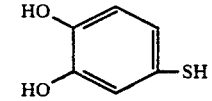 | $10^{-6}$ M | $2.10^{-6}$ M | $5.10^{-5}$ M | $2.10^{-5}$ M | $3.10^{-6}$ M |
| 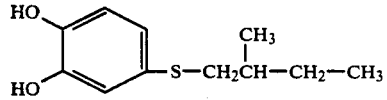 EXAMPLE 1 | $10^{-6}$ M | $10^{-5}$ M | $10^{-5}$ M | $5.10^{-5}$ M | $3.10^{-6}$ M |
| 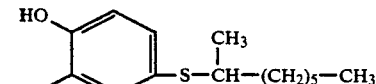 EXAMPLE 5 | $10^{-6}$ M | $2.10^{-6}$ M | $10^{-5}$ M | $2.10^{-6}$ M | $10^{-6}$ M |

Remarks

Stimulation of the 15-lipoxygenase by the above three compounds, at concentrations of $10^{-6}$M to $3 \times 10^{-6}$M is noted, whereas the 5-lipoxygenase is inhibited at these concentrations.

It will be noted that in experiment No. 1, the leucocytes have been stimulated by the ionophore alone whereas in experiment No. 2, the cells have been stimulated with ionophore and arachidonic acid. The presence of the arachidonic acid exogene augments by 10 times the ID$_{50}$ the inhibitors on the other hand, the addition of the arachidonic acid allows measurement of the activity of 15-lipoxygenase, normally not detectable in leucocytes stimulated by ionophore alone.

We claim:

1. A method of inhibiting lipoxygenase or cyclogenase in a subject in which the inhibition of same would be beneficial comprising the administration, in a pharmaceutically acceptable carrier, of a lipoxygenase or cyclogenese inhibiting amount of a catechol derivative having the general formula

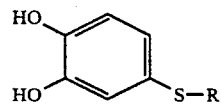

wherein R represents a straight or branched chain acyclic saturated hydrocarbon group having from 1 to 8 carbon atoms, one of which is optionally asymmetric, a mono- or bicycloalkyl group optionally substituted by one or more alkyl groups having from 1 to 7 carbon atoms, one of the carbon atoms of the mono- or bicycloalkyl group optionally being asymmetric, a phenyl group, a halophenyl group, a nitrophenyl group or a phenyl group substituted by one or more alkyl groups having from 1 to 7 carbon atoms or trifluoromethyl groups or COOY groups wherein Y stands for an alkyl having from 1 to 5 carbon atoms.

2. A pharmaceutical composition for inhibiting lipoxygenase or cyclogenase comprising a pharmaceutically acceptable carrier, and a lipoxygenase or cyclogenase inhibiting amount of a catechol derivative having the formula

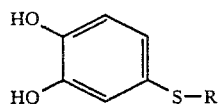

wherein R represents a straight or branched chain acyclic saturated hydrocarbon group having from 1 to 8 carbon atoms, one of which is optionally asymmetric, a mono- or bicycloalkyl group optionally substituted by one or more alkyl groups having from 1 to 7 carbon atoms, one of the carbon atoms of the mono- or bicycloalkyl group optionally being asymmetric, a phenyl group, a halophenyl group, a nitrophenyl group or a phenyl group substituted by one or more alkyl groups having from 1 to 7 carbon atoms or trifluoromethyl groups or COOY groups wherein Y stands for an alkyl having from 1 to 5 carbon atoms.

* * * * *

UNITED STATES PATENT AND TRADEMARK OFFICE
CERTIFICATE OF CORRECTION

PATENT NO. : 5,013,756
DATED : May 7, 1991
INVENTOR(S) : Michel Follet et al.

Page 1 of 2

It is certified that error appears in the above-identified patent and that said Letters Patent is hereby corrected as shown below:

Column 1, lines 25 and 29, change "asymetric" to --asymmetric--.

Column 2, line 2, change "STRITWIESER" to --STREITWIESER--.

Column 2, line 5, after "least" insert --one--.

Column 2, lines 47-48, change "1-2-methyl-butyl" to --ℓ-2-methyl-butyl--.

Column 3, lines 9 and 11, change "1-menthyl" to --ℓ-menthyl--.

Column 3, lines 47-48, change "1-1-methyl-heptyl" to --ℓ-1-methyl-heptyl--.

Column 3, line 66, change "164.C" to --164°C--.

Column 4, line 13, change "148.C" to --148°C--.

Column 5, line 7, change "dependant" to --dependent--.

Column 5, line 11, before "unit" insert --1--.

Column 5, line 36, change "sterioidal" to --steroidal--.

Column 6, line 21, change "leucocytes" to --leukocytes--.

Column 6, line 33, after "5996-5998" insert --;--.

Column 7, line 1 (before the table) insert --c. Results--.

Column 7, line 52, change "leucocytes" to --leukocytes--.

UNITED STATES PATENT AND TRADEMARK OFFICE
CERTIFICATE OF CORRECTION

PATENT NO. : 5,013,756
DATED : May 7, 1991
INVENTOR(S) : Michel Follet et al.

Page 2 of 2

It is certified that error appears in the above-identified patent and that said Letters Patent is hereby corrected as shown below:

Column 7, line 63, change "concomittant" to --concomitant--.

Column 10, line 29, change "Cycloxygenase" to --Cyclooxygenase--.

Column 11, line 24, after "sulphate" insert --.--.

Column 11, line 39 (in the table), change "Autoradiographes" to --Autoradiographs--.

Column 12, line 53, change "leucocytic" to --leukocytic--.

Column 12, line 58, change "leucocytes/ml." to --leukocytes/ml--.

Column 13, line 20, change "leucocytes/ml" to --leukocytes/ml--.

Column 13, lines 57-58, change "leucocytes" to --leukocytes--.

Column 13, line 62, after "inhibitors" insert --;--.

Column 13, line 65, change "leucocytes" to --leukocytes--.

Column 14, line 19, change "cyclogenese" to --cyclogenase--.

Signed and Sealed this

Sixth Day of October, 1992

*Attest:*

DOUGLAS B. COMER

*Attesting Officer*   *Acting Commissioner of Patents and Trademarks*